United States Patent [19]

Bayer et al.

[11] 4,056,581

[45] Nov. 1, 1977

[54] PROCESS FOR THE PREPARATION OF PHOSPHORODICHLORIDOTHIOLATES

[75] Inventors: Horst O. Bayer, Levittown; William S. Hurt, Collegeville, both of Pa.

[73] Assignee: Rohm and Haas Company, Philadelphia, Pa.

[21] Appl. No.: 607,078

[22] Filed: Aug. 22, 1975

[51] Int. Cl.$^2$ .............................................. C07F 9/20
[52] U.S. Cl. ................................. 260/972; 260/958; 260/960
[58] Field of Search ................................ 260/972, 960

[56] References Cited

U.S. PATENT DOCUMENTS 3,489,825 1/1970 Aichenegg .......................... 260/970

FOREIGN PATENT DOCUMENTS 446,510 12/1974 U.S.S.R.

OTHER PUBLICATIONS

Petrov et al, "Chem. Abs." vol. 55, (1961), 27018.
Phytopathology Res. Inst. Agdoc 43074, SU-395,372.

*Primary Examiner*—Anton H. Sutto

[57] ABSTRACT

Certain S-alkyl, -cycloalkyl, -aralkyl, and -aryl phosphorodichloridothiolates are prepared by reacting a sulfenyl chloride, which can be prepared in situ, with phosphorus trichloride and a carboxylic acid or water.

28 Claims, No Drawings

PROCESS FOR THE PREPARATION OF PHOSPHORODICHLORIDOTHIOLATES

The present invention relates to a process for preparing certain S-alkyl, -cycloalkyl, -aralkyl and -aryl phosphorodichloridothiolates. This novel proces involves reacting an alkyl, cycloalkyl, aralkyl or aryl sulfenyl chloride with phosphorus trichloride and a carboxylic acid or water to form the corresponding phosphorodichloridothiolates in high yield and purity under a variety of convenient and practical reaction conditions.

Known processes for preparing compounds of the present invention are disadvantageous because they are costly and time consuming and often result in contaminated end products, low yields, etc. For example, it is known that S-alkyl phosphorodichloridothiolates can be obtained by preparing the alkyl sulfenyl chloride via low temperature chlorination and subsequently adding the sulfenyl chloride to phosphorus trichloride, in excess liquid sulfur dioxide at $-50°$ C. However, the requirements of using low temperatures and excess sulfur dioxide are costly and time consuming and therefore severely limit the practicality of this process.

Accordng to the present invention, it has now been found that a practical and economical process can be provided for the production of certain S-alkyl, -cycloalkyl, -aralkyl, and -aryl phosphorodichloridothiolates. This process does not require the use of low temperatures or the malodorous and toxic sulfur dioxide, and results in compounds of high yield and purity.

The compounds produced by the process of this invention are useful as intermediates in the preparation of certain O,S-disubstituted phosphorochloridothiolates, which in turn are useful as intermediates in the preparation of known organophosphorus pesticides, such as those described in U.S. Pat. Nos. 3,374,293, 3,784,654, and 3,839,509 and in other patents too numerous to mention. The phosphorodichloridothiolates of the present invention can be converted to O,S-disubstituted phosphorochloridothiolates by various methods readily available to those skilled in the art. One method involves reaction the S-substituted phosphorodichloridothiolate with an alcohol in the presence of an acid scavenger, e.g. a tertiary amine, to produce the corresponding O,S-disubstituted phosphorochloridothiolate.

Among the compounds which can be prepared by the process of the present invention are those having the formula:

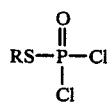  (I)

wherein R is
a. a ($C_1$–$C_{10}$) alkyl, preferably a ($C_1$–$C_7$) alkyl, most preferably a ($C_2$–$C_4$) alkyl group, optionally substituted with a ($C_1$–$C_4$) alkoxy group, preferably a methoxy or ethoxy group; a ($C_1$–$C_4$) alkylthio group, preferably a methylthio or ethylthio group; or a halogen atom, preferably a chlorine atom;
b. a ($C_3$–$C_6$) cycloalkyl group, preferably a cyclohexyl group;
c. a ($C_7$–$C_{10}$) aralkyl, preferably benzyl or phenethyl, group, optionally substituted with up to three ($C_1$–$C_5$) alkyl groups, preferably methyl groups; ($C_1$–$C_5$) alkoxy groups, preferably methoxy groups; halogen atoms, preferably chlorine atoms; or nitro groups; or
d. a ($C_6$–$C_{10}$) aryl, preferably phenyl, group, optionally substituted with up to three ($C_1$–$C_5$) alkyl groups, preferably methyl groups; ($C_1$–$C_5$) alkoxy groups, preferably methoxy groups; halogen atoms, preferably chlorine atoms; or nitro groups.

In a preferred embodiment of this invention, R is a ($C_1$–$C_7$) alkyl group, especially a ($C_2$–$C_4$) alkyl group.

As used in the specification and claims, the terms alkyl, alkoxy, alkylthio, and aralkyl refer to groups having a straight or branched chain spatial configuration.

The process of the present invention involves reacting a sulfenyl chloride of the formula:

wherein R is as defined for Formula I, with phosphorus trichloride and water or a carboxylic acid to give, via the transient phosphonium intermediate, a compound of Formula I.

Any carboxylic acid can be employed in the process of this invention; however a non-keto, non-aldo containing carboxylic acid is preferred, i.e. an acid other than a ketocarboxylic or aldocarboxylic is preferred.

The more preferred carboxylic acids can be represented by the formula:

wherein Y is a hydrogen atom; a ($C_1$–$C_8$) alkyl group optionally substituted with up to three halogen atoms, preferably chlorine atoms; or a group of the formula:

wherein X is a cyano group; a phenyl group optionally substituted with up to three ($C_1$–$C_5$) alkyl groups, preferably methyl groups, ($C_1$–$C_5$) alkoxy groups, preferably methoxy groups, halogen atoms, preferably chlorine atoms, or nitro groups; or a group of the formula:

wherein R' is a hydroxy group; a ($C_1$–$C_5$) alkoxy group; or a phenoxy group, optionally substituted with up to three ($C_1$–$C_5$) alkyl groups, preferably methyl groups, ($C_1$–$C_5$) alkoxy groups, preferably methoxy groups, halogen atoms, preferably chlorine atoms, or nitro groups; and n is an integer from 0 to 8.

The most preferred carboxylic acids can be represented by the formula:

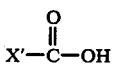

wherein X' is a ($C_1$–$C_6$) alkyl group, preferably a ($C_1$–$C_3$) alkyl group, or a phenyl group. Among the most preferred acids, acetic and propionic acids are more preferred, acetic acid being especially preferred.

The present process can be represented by the following reaction Scheme (A), which is presented for illustrative purposes only:

RSCl + PCl₃ → [RSPCl₄]

[RSPCl₄] + carboxylic acid or water →

RSPOCl₂ + acyl chloride + HCl or 2HCl wherein R is as defined above.

In the process represented by the foregoing Scheme, a carboxylic acid is preferred over water, since when a carboxylic acid is used, a valuable chemical intermediate, an acyl chloride, is obtained as a by-product. If desired, the acyl chloride obtained can be hydrolyzed to the corresponding carboxylic acid, which can then be used in additional syntheses of the compounds of this invention.

The preparative process can be carried out neat or with a solvent; however, the presence of an inert organic solvent is preferred. Suitable solvents include aromatic hydrocarbons such as benzene, toluene, and xylene; aromatic and aliphatic halogenated, especially chlorinated, hydrocarbons such as chlorobenzene, chloroform, carbon tetrachloride, and perchloroethylene; carboxylic acid esters such as ethyl acetate and butyl acetate; and the like. The preferred solvents are aromatic hydrocarbons and halogenated aromatic hydrocarbons, especially toluene, xylene, and chlorobenzene. The most preferred solvent is chlorobenzene.

The reaction is normally conducted at a temperature range of about −20° C to about 50° C. and preferably at about −5° C. to about 30° C. Generally, a substantially equimolar ratio of reactants is preferred, though up to 100% molar excesses of any of the reactants can be employed.

The reaction products are obtained by fractional distillation at reduced pressures or by other conventional techniques. The products thus obtained can be used in additional syntheses without further purification.

Typical examples of carboxylic acids which can be employed in the process of this invention are formic acid, acetic acid, propionic acid, butyric acid, isobutyric acid, benzoic acid, p-chlorobenzoic acid, chloropropionic acid, trichloroacetic acid, phenylacetic acid, cyanoacetic acid, oxalic acid-monomethyl ester, malonic acid, succinic acid, and the like.

According to the preferred process of this invention, the sulfenyl chloride of Scheme (A) is formed in situ by reacting the corresponding mercaptan (RSH) or disulfide (RSSR), preferably the mercaptan, with a chlorinating agent. This process is especially advantageous in that it can be carried out in a single continuous step without the isolation of any of the reactants or intermediates.

When a disulfide is employed in the formation of the sulfenyl chloride, the reactants, i.e., the disulfide, chlorinating agent, phosphorus trichloride and carboxylic acid or water, can be combined in any order. However, a preferred sequence involves (a) combining the disulfide, the phosphorus trichloride, and the carboxylic acid or water (preferably the carboxylic acid), and then (b) adding the chlorinating agent. A more preferred sequence involves (a) combining the disulfide and the carboxylic acid or water (preferably the carboxylic acid), (b) adding the chlorinating agent and then (c) adding the phosphorus trichloride.

When a mercaptan is employed in the formation of the sulfenyl chloride, the reactants can be combined in any order, provided that the chlorinating agent is added to the mercaptan before the phosphorus trichloride. A preferred sequence involves (a) combining the mercaptan and the carboxylic acid or water (preferably the carboxylic acid), (b) adding the chlorinating agent and then (c) adding the phosphorus trichloride. A more preferred sequence involves (a) adding the chlorinating agent to the mercaptan, (b) adding the carboxylic acid or water (preferably the carboxylic acid) and then (c) adding the phosphorus trichloride.

Reaction conditions such as choice of solvents and temperature correspond to the conditions described above for Scheme (A). Up to 100% molar excesses of any of the reagents can be employed, but the preferred molar ratios are as follows:

about 0.5 (RSSR) or about 1.0 RSH):

about 1.0 (PCl₃): about 1.0 – 1.5 (chlorinating agent)

Suitable chlorinating agents include chlorine, sulfuryl chloride, N-chlorosuccinimide and the like. Chlorine and sulfuryl chloride are more preferred, chlorine being most preferred.

The reaction products can be obtained by fractional distillation at reduced pressures or by other conventional techniques. The products obtained can be used in additional syntheses without further purification.

When the starting materials shown below in Columns I or II are utilized in the preferred process of this invention, the corresponding products shown in Column III are obtained.

I methyl disulfide
ethyl disulfide
n-propyl disulfide
isopropyl disulfide
n-butyl disulfide
isobutyl disulfide
sec-butyl disulfide
n-amyl disulfide
n-hexyl disulfide
n-decyl disulfide
2-(n-propoxyethyl) disulfide
2-methylthio-n-propyl disulfide
2-chloroethyl disulfide
cyclohexyl disulfide
benzyl disulfide
2-chlorophenethyl disulfide
phenyl disulfide
bis-2-methylphenyl disulfide
bis-4-ethylphenyl disulfide
bis-3,5-dimethyl-4-methoxyphenyl disulfide
bis-4-ethoxyphenyl disulfide
bis-3-bromophenyl disulfide
bis-4-chlorophenyl disulfide
bis-2,5-dichlorophenyl disulfide
bis-2,4,6-trichlorophenyl disulfide
bis-2,4-dichloro-6-methylphenyl disulfide
bis-2-chloro-4-propoxyphenyl disulfide
bis-2-chloro-4-bromophenyl disulfide
bis-4-fluorophenyl disulfide
bis-4-nitrophenyl disulfide
bis-2-nitro-4-chlorophenyl disulfide
bis-2-nitro-4-methylphenyl disulfide
bis-naphthyl disulfide
bis-3,5-dimethylnaphthyl disulfide
bis-3-chloronaphthyl disulfide
and the like.

II methyl mercaptan
ethyl mercaptan
n-propyl mercaptan
isopropyl mercaptan
n-butyl mercaptan
isobutyl mercaptan
sec-butyl mercaptan
n-amyl mercaptan
n-hexyl mercaptan
n-decyl mercaptan
2-(n-propoxyethyl) mercaptan
2-methylthio-n-propyl mercaptan
2-chloroethyl mercaptan
cyclohexyl mercaptan
benzyl mercaptan
2-chlorophenethyl mercaptan
thiophenol
2-methyl thiophenol
4-ethyl thiophenol
3,5-dimethyl-4-methoxy thiophenol
4-ethoxy thiophenol
3-bromo thiophenol
4-chloro thiophenol
2,5-dichloro thiophenol
2,4,6-thrichloro thiophenol
2,4-dichloro-6-methyl thiophenol
2-chloro-4-propoxy thiophenol
2-chloro-4-bromo thiophenol
4-fluoro thiophenol
4-nitro thiophenol
2-nitro-4-chloro-thiophenol
2-nitro-4-methyl thiophenol
naphthyl mercaptan
3,5-dimethylnaphthyl mercaptan
3-chloronaphthyl mercaptan
and the like.

III

S-methyl phosphorodichloridothiolate
S-ethyl phosphorodichloridothiolate
S-n-propyl phosphorodichloridothiolate
S-isopropyl phosphorodichloridothiolate
S-n-butyl phosphorodichloridothiolate
S-isobutyl phosphorodichloridothiolate
S-sec-butyl phosphorodichloridothiolate
S-n-amyl phosphorodichloridothiolate
S-n-hexyl phosphorodichloridothiolate
S-n-decyl phosphorodichloridothiolate
S-2-(n-propoxyethyl)phosphorodichloridothiolate
S-2-methylthio-n-propyl phosphorodichloridothiolate
S-2-chloroethyl phosphorodichloridothiolate
S-cyclohexyl phosphorodichloridothiolate
S-benxyl phosphorodichloridothiolate
S-2-chloro-phenethyl phosphorodichloridothiolate
S-phenyl phosphorodichloridothiolate
S-(2-methylphenyl) phosphorodichloridothiolate
S-(4-ethylphenyl) phosphorodichloridothiolate
S-(3,5-dimethyl-4-methoxyphenyl) phosphorodichloridothiolate
S-(4-ethoxyphenyl) phosphorodichloridothiolate
S-(3-bromophenyl) phosphorodichloridothiolate
S-(4-chlorophenyl) phosphorodichloridothiolate
S-(2,5-dichlorophenyl) phosphorodichloridothiolate
S-(2,4,6-trichlorophenyl) phosphorodichloridothiolate
S-(2,4-dichloro-6-methylphenyl) phosphorodichloridothiolate
S-(2-chloro-4-propoxyphenyl) phosphorodichloridothiolate
S-(2-chloro-4-bromophenyl) phosphorodichloridothiolate
S-(4-fluorophenyl) phosphorodichloridothiolate
S-(4-nitrophenyl) phosphorodichloridothiolate
S-(2-nitro-4-chlorophenyl) phosphorodichloridothiolate
S-(2-nitro-4-methylphenyl) phosphorodichloridothiolate
S-naphthyl phosphorodichloridothiolate
S-(3,5-dimethylnaphthyl) phosphorodichloridothiolate
S-(3-chloronaphthyl) phosphorodichloridothiolate
and the like.

All of the starting materials used in the preparation of the compounds of this invention are known compounds or are readily prepared by methods available to those skilled in the art.

The following examples, I to XV, illustrate, without limitation of the scope of the present invention, variations of the preferred process of this invention. Example XVI illustrates the preparation of an O,S-disubstituted phosphorochloridothiolate from a phosphorodichloridothiolate of the present invention.

EXAMPLE I

To a stirring solution of 76.7 g. (0.51 mole) of n-propyl disulfide in 200 g. of dry toluene is added, over a six minute period, 137.3 g. (1.0 mole) of phosphorus trichloride at 0°–3° C. Glacial acetic acid, 60.1 g. (1.0 mole), is added to this solution over a 7 minute period and the solution is stirred for an additional 11 minutes at 2° C. Next, 67.5 g. (0.5 mole) of sulfuryl chloride is added at 2° C. over a 33 minute period. The stirring solution is held an additional 15 minutes at 2°–3° C. after which an additional 33.8 g. (0.25 mole) of sulfuryl chloride is added. The solution is allowed to warm slowly (1.5 hours) to room temperature and held for an additional 1.5 hours at 22° C.

The solution is then concentrated in vacuo (ca 20 mm. Hg) for 30 minutes at 50° C. and the lower boiling fraction (255 g. of toluene and acetyl chloride) is collected in a dry ice trap. The residue, 194 g. (100%) of the crude phosphorodichloridothiolate, is fractionally distilled to give 174 g. (90%) of the pure S-n-propyl phosphorodichloridothiolate as the middle fraction, b.p. 40°–50° C., 0.07 – 0.27 mm.

Anal. calc'd. (found) for $C_3H_7Cl_2OPS$: C, 18.7 (18.7); H, 3.66 (3.63); Cl, 36.7 (36.9); P, 16.0 (16.2); S, 16.6 (16.6).

This lower boiling fraction is redistilled at atmospheric pressure to give 57.5 g. (73%) of acetyl chloride, b.p. 49°–51° C. as the middle fraction.

EXAMPLE II

To a stirring solution of 76.7 g. (0.51 mole) of n-propyl disulfide in 200 g. of dry toluene is added over a six minute period, 137.3 g. (1.0 mole) of phosphorus trichloride at 0°–3° C. Glacial acetic acid, 60.1 g. (1.0 mole) is added to this solution over a 7 minute period and the solution is stirred for an additional 11 minutes at 2° C. Next, a stream of chloride gas is bubbled in at a flow rate of 71 grams per hour while maintaining a temperature of −5° to 8° C. After 55.4 g. (0.78 mole) of chlorine is added, the solution is allowed to warm to room temperature and stripped in vacuo (40° C., 15 minutes) to remove the toluene and acetyl chloride. The residue, 154.1 g, is fractionally distilled to give 130.6 g. (72%) of S-n-propyl phosphorodichloridothiolate.

EXAMPLE III

To a stirring solution of 75.2 g. (0.5 mole) of n-propyl disulfide in 200 g. of dry toluene is added over a 3 minute period, 137.3 g. (1.0 mole) of phosphorus trichloride at −3° to 0° C. Then, propionic acid, 74.1 g. (1.0 mole), is added over a 4 minute period after which 83.5 g. (0.6 mole) of sulfuryl chloride is added at −5° to 5° C. over a 26 minute period.

The solution is held at 8° C. for two hours and then concentrated in vacuo (40°–45° C./20 mm.). The volatiles, 305 g. of toluene and propionyl chloride, are collected in a dry ice trap. The residue is fractionally distilled to give 168 g. (88%) of S-n-propyl phosphorodichloridothiolate.

The lower boiling fraction is redistilled at atmospheric pressure to give 67.6 g. (74%) of propionyl chloride.

EXAMPLE III (A)

The process described in Example III is repeated with the exceptions that chlorine gas [60.7 g., 0.86 mole (a 72% excess)] is substituted for the sulfuryl chloride (no attempt is made to isolate the acyl chloride). The yield of S-n-propyl phosphorodichloridothiolate is 79%.

EXAMPLE III (B)

The process described in Example III (a) is repeated with the exceptions that 1.1 mole (a 10% excess) of phosphorus trichloride and 0.81 mole (a 60% excess) of chlorine are used. The yield of S-n-propyl phosphorodichloridothiolate is 71%.

EXAMPLE III (C)

The process described in Example III (a) is repeated with the exception that 1.1 moles (a 10% excess) of propionic acid is used. The yield of S-n-propyl phosphorodichloridothiolate is 79%.

EXAMPLE III (D)

The process described in Example III (a) is repeated with the exception that 233 g. of carbon tetrachloride is used in place of the toluene. The yield of S-n-propyl phosphorodichloridothiolate is 79%.

EXAMPLE IV

To a stirring solution of 75.2 g. (0.5 mole) of n-propyl disulfide and 74.1 g. (1.0 mole) of propionic acid in 200 ml. of dry toluene at −4° C., is added 69.5 g. (0.5 mole) of sulfuryl chloride over a six minute period. Then, 137.3 g. (1.0 mole) of phosphorus trichloride is added dropwise with stirring at 0°–5° C. over a period of 15 minutes. The solution is held for two hours at 0° C. Analysis by glc indicates only 97% completion so an additional 3.5 g. (0.025 mole) of sulfuryl chloride is added and the solution is then held at 0° C for an additional 1 1/2 hours. The solution is then concentrated in vacuo (40°–70° C., 25 mm.) to give 187.4 g. (98%) of S-n-propyl phosphorodichloridothiolate.

EXAMPLE IV (A)

The process described in Example IV is repeated with the exception that 52.2 g. (0.736 mole) of chlorine is used in place of the sulfuryl chloride. The yield is 175.6 g. (91%) of S-n-propyl phosphorodichloridothiolate.

EXAMPLE V

To a solution of 15.0 g. (0.1 mole) of n-propyl disulfide and 27.5 g. (0.2 mole) of phosphorus trichloride in 100 ml. of carbon tetrachloride is added, with stirring, a solution of 20.9 g. (0.15 mole) of sulfuryl chloride at 0° C. over a period of 10 minutes. Then, 12.0 g. (0.2 mole) of glacial acetic acid is added dropwise with stirring at 0°–11° C. over a period of 15 minutes. The solvent and acetyl chloride are then removed in vacuo to give 31.0 g. (72%) of S-n-propyl phosphorodichloridothiolate.

EXAMPLE VI

Phosphorus trichloride, 6.9 g. (0.05 mole), is added neat to 3.75 g. (0.025 mole) of neat n-propyl disulfide at room temperature. Then, 3.0 g. (0.050 mole) of glacial acetic acid is added dropwise at room temperature, followed by 7.8 g. (0.038 mole) of neat sulfuryl chloride at room temperature. The acetyl chloride is then removed in vacuo and the residue (7.8 g.) distilled to give 6.8 g. (70%) of the pure S-n-propyl phosphorodichloridothiolate.

EXAMPLE VII

To a solution of 15.3 g. (0.102 mole) of n-propyl disulfide and 27.5 g. (0.2 mole) of phosphorus trichloride in 47 ml. of dry toluene is added 13.8 g. (0.102 mole) of sulfuryl chloride at −2° to 2° C. Then, 3.6 g. (0.2 mole) of deionized water is added at a rate of 0.4 g./3 min. while maintaining a temperature of −1° to 6° C. At the conclusion of the addition, the reaction is concentrated in vacuo and shown by glc analysis to be an 81:19 mixture of S-n-propyl phosphorodichloridothiolate and n-propyl disulfide.

EXAMPLE VIII

To a cold (−15° C.) solution of 12.2 g. (0.1 mole) of ethyl disulfide in 100 ml. of carbon tetrachloride is added, with stirring, 13.8 g. (0.1 mole) of sulfuryl chloride in 50 ml. of carbon tetrachloride. The solution is allowed to warm to 0° C. and then added dropwise with stirring to a cold (0°–3° C.) solution of 12.0 g. (0.2 mole) of acetic acid and 27.6 g. (0.2 mole) of phosphorus trichloride in 100 ml. of carbon tetrachloride. After stirring overnight at room temperature, the solvent and acetyl chloride are removed in vacuo and the residue, 36.3 g., is distilled (b.p. 43° C./0.15 mm.) to give 33.6 g. (94%) of S-ethyl phosphorodichloridothiolate. Analysis calc'd (found) for $C_2H_5Cl_2OPS$: C, 13.4 (13.6); H, 2.81 (2.93).

EXAMPLE IX

To a cold (−15° C.) solution of 100 g. (0.56 mole) of isobutyl disulfide in 300 ml. of carbon tetrachloride is added, with stirring, 76 g. (0.56 mole) of sulfuryl chloride in 150 ml. of carbon tetrachloride. The solution is allowed to warm to 25° C. over a period of 1.5 hours after which it is added slowly, with stirring, to a cold (−6° C.) solution of 137.3 g. (1.12 moles) of phosphorus trichloride in 300 ml. of carbon tetrachloride and allowed to stand overnight at room temperature. Then, 69.2 g. (1.12 moles) of glacial acetic acid is added dropwise with stirring at −5° C. The solution is allowed to warm to room temperature, held there for two hours and then concentrated in vacuo to give 143.7 g. of the crude phosphorothiolate as a yellow oil. Fractional distillation gives, as the middle fraction, 94.7 g. (82% yield) of the pure S-isobutyl phosphorodichloridothiolate, b.p. 48°-50° C./0.2 mm.

EXAMPLE X

To a stirring solution of 17.8 g. (0.1 mole) of isobutyl disulfide in 50 ml. of carbon tetrachloride is added at 0°-5° C., a solution of 27.46 g. (0.2 mole) of phosphorus trichloride in 50 ml. of carbon tetrachloride followed by a solution of 12.0 g. (0.2 mole) of glacial acetic acid in 50 ml. of carbon tetrachloride. Then, sulfuryl chloride, 16.5 g. (0.12 mole) in 50 ml. of carbon tetrachloride is added over a 20 minute period at 0°-5° C. The solution is allowed to stir overnight at room temperature and then concentrated in vacuo to give 41.6 g. of the crude S-isobutyl phosphorodichloridothiolate. Fractional distillation gives the pure S-isobutyl phosphorodichloridothiolate as the middle fraction, b.p. =55°-57° C./0.05 mm. Analysis calc'd (found) for $C_4H_9Cl_2OPS$: C, 23.2 (23.2) H, 4.38 (4.64).

According to the procedure of Example X, the following compounds (Examples XI and XII) are similarly prepared:

EXAMPLE XI

S-sec-butyl phosphorodichloridothiolate, b.p. = 51.5-56.5/0.015 mm.

Analysis calc'd. (found) for $C_4H_9Cl_2OPS$: C, 23.2 (23.9); H, 4.38 (4.70).

EXAMPLE XII

S-n-butyl phosphorodichloridothiolate, b.p.= 64-67/0.2 mm.

Analysis calc'd (found) for $C_4H_9Cl_2OPS$: C, 23.2(23.6); H, 4,38 (4.52).

EXAMPLE XIII

To a stirring solution of 76.0 g. (1.0 mole) of n-propyl mercaptan in 300 ml. of toluene is added at −3° to 7° C., 80.4 g. (1.13 moles) of chlorine over a period of 37 minutes. Then 60.0 g. (1.0 mole) of acetic acid is added in one portion at −3° C., followed by 137.3 g. (1.0 mole) of phosphorus trichloride added dropwise at −3 to 6° C. over a period of one hour. The solution is stirred for 1½ hours at 12° C., and then the solvent is removed in vacuo to give S-n-propyl phosphorodichloridothiolate.

EXAMPLE XIV

To a stirring solution of 76.0 g. (1.0 mole) of n-propyl mercaptan in 300 ml. of toluene is added at −3° to 7° C., 148 g. (1.1 moles) of sulfuryl chloride dropwise over a period of 37 minutes. Then 74.1 g. (1.0 mole) of propionic acid is added in one portion at −3° C., followed by 137.3 g. (1.0 mole) of phosphorus trichloride added dropwise at −3° to 6° C. over a period of one hour. The solution is stirred for 1½ hours at 12° C., an additional 3.0 ml. of sulfuryl chloride is added, and then the solvent is removed in vacuo to give 176 g. (92%) of S-n-propyl phosphorodichloridothiolate.

EXAMPLE XV

To a stirring solution of 148 g. (1.1 moles) of sulfuryl chloride in 250 ml. of toluene a solution of 76 g. (1.0 mole) of n-propyl mercaptan in 60 ml. of toluene is added dropwise over a period of 36 minutes. Propionic acid, 74.1 g. (1.0 mole) is added in a single portion and then 137.6 g. (1.0 mole) of phosphorus trichloride is added dropwise at 0°-8° C. over a period of one hour. After one-half hour at 9° C., an additional 4 g. of sulfuryl chloride is added to insure completion of the reaction. After an additional hour at 15°-30° C., the reaction is concentrated in vacuo to give 179.7 g. (93%) of S-n-propyl phosphorodichloridothiolate.

EXAMPLE XVI

To a stirring solution of 50.0 g. (0.26 mole) of S-n-propyl phosphorodichloridothiolate in 200 ml. of a 3:1 benzene-hexane mixture is added a mixture of 11.9 g. (0.26 mole) of ethanol and 26.2 g. (0.26 mole) of triethyl amine in 50 ml. of benzene. The temperature is maintained at 0°-5° C. during the dropwise addition and then allowed to slowly warm to room temperature. After standing overnight, the mixture is filtered to remove triethyl amine hydrochloride, passed through a short column of silicic acid (30 g.) and concentrated in vacuo to give 41.5 g. (79%) of O-ethyl S-n-propyl phosphorochloridothiolate, b.p. = 58° C./0.2 mm. The compound is identified by comparison with a known sample of O-ethyl S-n-propyl phosphorochloridothiolate, prepared by the method of Lippman [J. Org. Chem., 30 (1965)].

It will be appreciated that the instant specification and examples are set forth by way of illustration and not limitation, and that various modifications and changes may be made without departing from the spirit and scope of the present invention.

We claim:
1. A process for preparing a phosphorodichloridothiolate of the formula

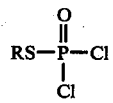

wherein R is
   a. a ($C_1$-$C_{10}$) alkyl group, optionally substituted with a ($C_1$-$C_4$) alkoxy group, a ($C_1$-$C_4$) alkylthio group or a halogen atom;
   b. a ($C_3$-$C_6$)cycloalkyl group;
   c. a ($C_7$-$C_{10}$) aralkyl group, optionally substituted with up to three ($C_1$-$C_5$) alkyl groups, ($C_1$-$C_5$) alkoxy groups, halogen atoms, or nitro groups; or
   d. a ($C_6$-$C_{10}$) aryl group, optionally substituted with up to three ($C_1$-$C_5$) alkyl groups, ($C_1$-$C_5$) alkoxy groups, halogen atoms or nitro groups;
which comprises reacting at a temperature of about −20° C. to about 50° C., a sulfenyl chloride of the formula

wherein R is as defined above,
with phosphorus trichloride, and water or a carboxylic acid.

2. A process according to claim 1 wherein the sulfenyl chloride is formed in situ by reacting a disulfide of the formula, RSSR, with a chlorinating agent.

3. A proces according to claim 2 wherein the reaction is carried out in the presence of an inert organic solvent.

4. A process according to claim 3 wherein the solvent is an aromatic hydrocarbon, an aromatic or aliphatic halogenated hydrocarbon, or a carboxylic acid ester.

5. A process according to claim 4 wherein the reaction is carried out at a temperature range of about −5° C. to about 30° C.

6. A process according to claim 5 wherein the carboxylic acid has the formula

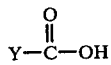

wherein Y is a hydrogen atom; a (C$_1$-C$_8$) alkyl group optionally substituted with up to three halogen atoms; or a group of the formula X-(CH$_2$)$_n$— wherein X is a cyano group; a phenyl group optionally substituted with up to three (C$_1$-C$_5$) alkyl groups, (C$_1$-C$_5$) alkoxy groups, halogen atoms, or nitro groups; or a group of the formula

wherein R' is a hydroxy group; a (C$_1$-C$_5$) alkoxy group; or a phenoxy group, optionally substituted with up to three (C$_1$-C$_5$) alkyl groups, (C$_1$-C$_5$) alkoxy groups, halogen atoms, or nitro groups; and n is an integer from 0 to 8.

7. A process according to claim 6 wherein the chlorinating agent is chlorine or sulfuryl chloride.

8. A process according to claim 7 wherein R is a (C$_1$-C$_7$) alkyl group.

9. A process according to claim 8 wherein R is a (C$_2$-C$_4$) alkyl group.

10. A process according to claim 9 wherein the carboxylic acid has the formula

wherein X' is a (C$_1$-C$_6$) alkyl group or a phenyl group.

11. A process according to claim 10 wherein the chlorinating agent is added to a combination of the phosphorus trichloride, the disulfide, and the carboxylic acid.

12. A process according to claim 11 wherein about 1.0 to 1.5 moles of chlorinating agent are added to a combination of about 1.0 mole of phosphorus trichloride, about 0.5 mole of disulfide, and about 1.0 mole of carboxylic acid.

13. A process according to claim 10 wherein the chlorinating agent is added to a combination of the disulfide and the carboxylic acid, and then the phosphorus trichloride is added.

14. A process according to claim 13 wherein about 1.0 to 1.5 moles of chlorinating agent are added to a combination of about 0.5 mole of disulfide and about 1.0 mole of carboxylic acid, and then about 1.0 mole of phosphorus trichloride is added.

15. A process according to claim 1 wherein the sulfenyl chloride is formed in situ by reacting a mercaptan of the formula, RSH, with a chlorinating agent prior to addition of the phosphorus trichloride.

16. A process according to claim 15 wherein the reaction is carried out in the presence of an inert organic solvent.

17. A process according to claim 16 wherein the solvent is an aromatic hydrocarbon, an aromatic or aliphatic halogenated hydrocarbon, or a carboxylic acid ester.

18. A process according to claim 17 wherein the reaction is carried out at a temperature range of about −5° C. to about 30° C.

19. A process according to claim 18 wherein the carboxylic acid has the formula

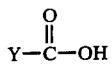

wherein Y is a hydrogen atom; a (C$_1$-C$_8$) alkyl group optionally substituted with up to three halogen atoms; or a group of the formula X—(CH$_2$)$_n$— wherein X is a cyano group; a phenyl group optionally substituted with up to three (C$_1$-C$_5$) alkyl groups, (C$_1$-C$_5$) alkoxy groups, halogen atoms, or nitro groups; or a group of the formula

wherein R' is a hydroxy group; a (C$_1$-C$_5$) alkoxy group; or a phenoxy group, optionally substituted with up to three (C$_1$-C$_5$) alkyl groups, (C$_1$-C$_5$) alkoxy groups, halogen atoms, or nitro groups; and n is an integer from 0 to 8.

20. A process according to claim 19 wherein the chlorinating agent is chlorine or sulfuryl chloride.

21. A process according to claim 20 wherein R is a (C$_1$-C$_7$) alkyl group.

22. A process according to claim 21 wherein R is a (C$_2$-C$_4$) alkyl group.

23. A process according to claim 22 wherein the carboxylic acid has the formula

wherein X' is a (C$_1$-C$_6$) alkyl group or a phenyl group.

24. A process according to claim 23 wherein the chlorinating agent is added to a combination of the mercaptan and the carboxylic acid.

25. A process according to claim 24 wherein about 1.0 to about 1.5 moles of chlorinating agent are added to a combination of about 1.0 mole of mercaptan and about 1.0 mole of carboxylic acid, and then about 1.0 mole of phosphorus trichloride is added.

26. A process according to claim 23 wherein the chlorinating agent is added to the mercaptan, then the carboxylic acid is added, followed by the addition of the phosphorus trichloride.

27. A process according to claim 26 wherein about 1.0 to 1.5 moles of chlorinating agent are added to about 1.0 mole of mercaptan, then about 1.0 mole of carboxylic acid is added, followed by the addition of about 1.0 mole of phosphorus trichloride.

28. A process according to claim 27 wherein the chlorinating agent is chlorine, the carboxylic acid is acetic acid, and the mercaptan is n-propyl mercaptan.

* * * * *